United States Patent [19]

Nazerian et al.

[11] Patent Number: 5,369,025
[45] Date of Patent: Nov. 29, 1994

[54] RECOMBINANT FOWLPOX VACCINE FOR PROTECTION AGAINST MAREK'S DISEASE

[75] Inventors: Keyvan Nazerian, Haslett; Lucy F. Lee, East Lansing; Noboru Yanagida, East Lansing; Ryohei Ogawa, East Lansing; Yi Li, East Lansing, all of Mich.

[73] Assignees: The United States of America as represented by the Secretary of Agriculture, Washington, D.C.; Nippon Zeon Co., Ltd., Tokyo, Japan

[21] Appl. No.: 803,633

[22] Filed: Dec. 10, 1991

Related U.S. Application Data

[63] Continuation-in-part of Ser. No. 722,860, Jun. 28, 1991, abandoned.

[51] Int. Cl.$^5$ .................. C12N 7/00; C12N 15/00; C12P 21/02; C12P 19/34
[52] U.S. Cl. .................. 435/235.1; 435/69.3; 435/172.3; 435/240.2; 536/23.72; 424/186.1; 424/199.1; 424/229.1; 530/350; 935/9; 935/32; 935/34; 935/57; 935/63; 935/65; 935/70
[58] Field of Search .................. 435/69.3, 91, 172.3, 435/235.1, 240.2; 530/350; 424/89; 935/9, 32, 34, 57, 63, 65, 70; 536/27

[56] References Cited

U.S. PATENT DOCUMENTS 5,021,347 6/1991 Yasui et al. .................. 435/235.1

FOREIGN PATENT DOCUMENTS

| | | | |
|---|---|---|---|
| 24458/88 | 5/1989 | Australia | C12N 7/04 |
| 0284416 | of 1988 | European Pat. Off. | C12N 15/00 |
| 0314569 | 3/1989 | European Pat. Off. | C12N 15/00 |
| WO89/12684 | 12/1989 | WIPO | C12N 15/00 |
| 90/02803 | 3/1990 | WIPO | C12N 15/38 |

OTHER PUBLICATIONS

Lewin Science vol. 237 (1987) Sep. 25, 1987.
Reeck et al. Cell vol. 50 Aug. 28, 1987.
Churchill et al, Nature, vol. 221, pp. 744–747 (1969).
Schat et al, J. Natl. Cancer Inst., vol. 60, No. 5, pp. 1075–1081 (1978).
Blacklaws et al, Virology, 177:727–736 (1990).
Boyle et al, Virus Research, vol. 10, pp. 343–356 (1988).
Ogawa et al, Vaccine, vol. 8, pp. 486–490 (1990).
Okazaki et al, "Protection Against Marek's Disease by Vaccination with a Herpesvirus of Turkeys", pp. 413–429 (1970).
Rispens et al, "Control of Marek's Disease in the Netherlands . . . Laboratory Vaccination Trials", pp. 108–125.
Witter et al, Avian Pathology, 8:145–156 (1979).
Yuen et al, Proc. Natl. Acad. Sci. USA, vol. 84, pp. 6417–6421 (1987).
Sanger et al, Proc. Natl. Acad. Sci. USA, vol. 74, No. 12, pp. 5463–5467 (1977).
Tsurushita et al, Gene, 62:135–139 (1988).
Shirakawa et al, Gene, 28:127–132 (1984).
Silva et al, Virology, vol. 136, pp. 307–320 (1984).
Ross et al, J. gen. Virol., 70:1789–1804 (1989).
Yanagida et al, Journal of Virology, vol. 66, No. 3, pp. 1402–1408 (1992).
Nazerian et al, Journal of Virology, vol. 66, No. 3, pp. 1409–1413 (1992).
Ross et al, Journal of General Virology, vol. 72, No. 4, pp. 939–947 (1991).
Proceedings XIX World's Poultry Congress, Amsterdam, The Netherlands, (1992), vol. 1, pp. 144–149.
Davison et al. *J. Mol. Biol.*(1980) 210, 771–784.
Davison et al. *J. Mol. Biol.* (1980) 210, 749–769.

*Primary Examiner*—Joan Ellis
*Attorney, Agent, or Firm*—Birch, Stewart, Kolasch & Birch

[57] ABSTRACT

A recombinant fowlpox virus is disclosed which is useful as a vaccine for protection against Marek's Disease. The recombinant virus preferably contains a gene for one or more Marek's Disease Virus antigens such as glycoprotein B homologue, glycoprotein C homologue, glycoprotein D homologue, glycoprotein H homologue and tegument proteins, under the control of a poxvirus promoter within a region of the DNA of fowlpox virus which is not essential for virus growth.

**

```
SEQ.
ID. NO.                    FPV promoter                                    start
  1     5'-AATTCGAGCTCGGATCGTTGAAAAATATAGATCCTAAAATGGAA              -3'
  2     3'-    GCTCGAGCCTAGCAACTTTTTATTATATCTAGGATTTTACCTTCTAG-5'
             EcoRI 3     5'-AGCTTTTTTTTTTTTTTTTGGCATATAAATAATAAATACAATAATTAATTA              -3'
  4     3'-    AAAAAAAAAAAAAAAACCGTATATTTATTATTTATGTTATTAATTAATTAATGCGC-5'
             HindIII                                                   MluI 5     5'-CGCGTAAAAATTGAAAACTATTCTAATTTATTGCACTCG              -3'
  6     3'-    ATTTTTAACTTTTTGATAAGATTAAATAACGTGAGCCTAG-5'
             MluI                                     BamHI 7     5'-GATCCCCGGGCGAGCTCGCTAGCGGGGCCCATGCGGTACCG              -3'
  8     3'-    GGGCCCGCTCGAGCGATCGCCCGGGCTACGCCATGGCCTAGGCAGCT-5'
             BamHI  SmaI  SacI  NheI  ApaI  SphI  KpnI  SalI both directional terminator
  9     5'-TCGACCCGGTACATTTTTATAAAAATGTACCCGGGGATC-3'
 10     3'-    GGGCCATGTAAAAATATTTTTACATGGGCCCCTAG-5'
```

FIG. 2

RECOMBINANT FOWLPOX VACCINE FOR PROTECTION AGAINST MAREK'S DISEASE

CROSS REFERENCE TO RELATED APPLICATIONS

This application is a continuation-in-part of copending application Ser. No. 07/722,860 filed on Jun. 28, 1991, now abandoned, the entire contents of which are hereby incorporated by reference.

BACKGROUND OF THE INVENTION

1. Field of the Invention

The present invention relates to a vaccine that protects against Marek's disease.

2. Description of Related Art

Marek's disease (MD) is a highly contagious neoplastic disease of domestic chicken that affects chickens worldwide and causes high mortality and condemnation if the chickens are not vaccinated at one day of age. MD is caused by a highly cell-associated oncogenic herpesvirus known as Marek's disease virus (MDV).

A number of live virus cell-associated vaccines are available that protect chickens against MD. These vaccines are maintained and administered in delicate cell-associated form. The vaccines need special handling and must be stored and transported in a frozen state in liquid nitrogen in order to maintain their viability and efficacy. These existing vaccines must be maintained and administered in cell-associated form, a condition that is costly and cumbersome.

The known vaccines contain the entire MDV genome, including sequences related to induction of pathogenesis. Although the existing vaccines against MD are either attenuated or are naturally apathogenic, viral mutation is known to occur in herpesviruses and there is a possibility that virulent pathogenic mutants may emerge in such vaccines. Such mutants could be less effective and even harmful.

Churchill et al, Nature, 221:744–747 (1969) and Okazaki et al, Arian Dis., 14:413–429 (1970) developed the first effective and safe vaccines against MD. These vaccines have been in use for the last 20 years and have reduced losses to the poultry industry worldwide. Other candidate vaccines based on serotype 2 naturally apathogenic MDV, Schat et al, J. Natl. Cancer Inst., 60, 1075–1082 (1978), or newly attenuated serotype 1 MDV, Rispens et al, Arian Dis., 16:108–125 (1972), and combinations of these viruses as bivalent vaccines, Witter, Arian Dis., 31:252–257 (1987), have helped provide a better protection against MD. All these vaccines, except the herpesvirus of turkeys (HVT) vaccine, require the storage and transportation in frozen state in liquid nitrogen and have to be administered as infected cells which calls for careful procedures to prevent inactivation of the vaccine. Even in the case of HVT vaccine, cell-associated viruses have been most widely used because they are more effective than cell-free virus in the presence of maternal antibodies, Witter et al, Avian Pathol., 8:145–156 (1978).

Recombinant DNA technology has allowed the construction of recombinant vaccines that contain only those desired viral genes or gene products that induce immunity without exposing the animal to genes that may induce pathological disorders. Pox viruses, including avipox virus, especially the fowlpox virus (FPV), provide excellent models for such vaccines. These viruses have a large DNA molecule with numerous non-essential regions that allow the insertion of several immunogenic genes into the same virus for the purpose of creating multivalent vaccines. These multivalent vaccines may induce cell-mediated as well as antibody-mediated immune response in a vaccinated host. Vaccinia virus (W) has been used extensively for this purpose and a number of VW recombinants have been constructed that express a variety of foreign genes including those that elicit neutralizing antibodies against glycoproteins of herpes simplex virus (HSV) type 1, Blacklaws et al, Virology, 177:727–736 (1990). Similarly, there are a number of reports describing the expression of foreign genes by recombinant FPV, Boyle et al, Virus Res., 10:343–356 (1988) and Ogawa et al, Vaccine, 8:486–490 (1990).

MDV homologues of the HSV gene coding for glycoproteins B, C, D, H, and I (gBh, gCh, gDh, gHh and gIh) have recently been cloned and sequenced, Coussens et al, J. Virol., 62:2373–2379 (1988), Ross et al, J. Gen. Virol., 70:1789–1804 (1989), Ross et al, J. Gen. Virol., 72:939–947 (1991), Ross et al, European Patent Application International Publication No. WO 90/02803 (1990).

SUMMARY OF THE INVENTION

It is an object of the present invention to provide a novel, effective, and safe vaccine against MD that exposes and immunizes the chicken only to the immunogenic gene product(s) of the MDV without exposure to its pathogenic gene products. The novel vaccine of the present invention, that lacks sequence related to pathogenic elements of MDV, is available in cell-free form and induces effective immunity against virulent MD. This is far more desirable than the existing vaccines.

It is also an object of the invention to provide cell-free vaccine against MD containing recombinant (rec) FPV that can be lyophilized, stored, and used under normal conditions thereby obviating costly and laborious procedures of storing the vaccine in liquid nitrogen, delicate handling, and administering which are necessary with existing cell-associated MD vaccines. For example, the vaccine of the present invention, after lyophilization, can be stored, handled, and transported at ambient temperature (20°–22° C.) and stored at 4° C. for prolonged periods of time. The vaccine can also be stored in a frozen state wherein the cell-free recombinant virus is present in an aqueous solution which is frozen and stored at, for example, −20° C. or −70° C.

This invention relates to the development of a novel recombinant FPV vaccine that contains a gene which encodes a glycoprotein B homologue (gBh) of MDV, expresses this gBh gene in cell culture and provides a strong protection against MD in the natural host (chicken), when administered as a cell-free material. In addition, the vaccine will also protect against fowlpox.

A further object of the invention is to provide recombinant FPV vaccines against MD in which gBh gene of MDV as well as other MDV genes such as those coding for glycoprotein C homologue, glycoprotein D homologue, tegument proteins and glycoproteins from different serotypes of MDV are inserted into FPV for the purpose of creating a broad-spectrum vaccine effective against several isolates of MDV.

BRIEF DESCRIPTION OF THE DRAWINGS

FIG. 2 shows the sequences of 10 oligonucleotides (SEQ. ID. NOS. 1–10) used for construction of pNZ1729R insertion vector;

DETAILED DESCRIPTION OF THE INVENTION

Figure 1:
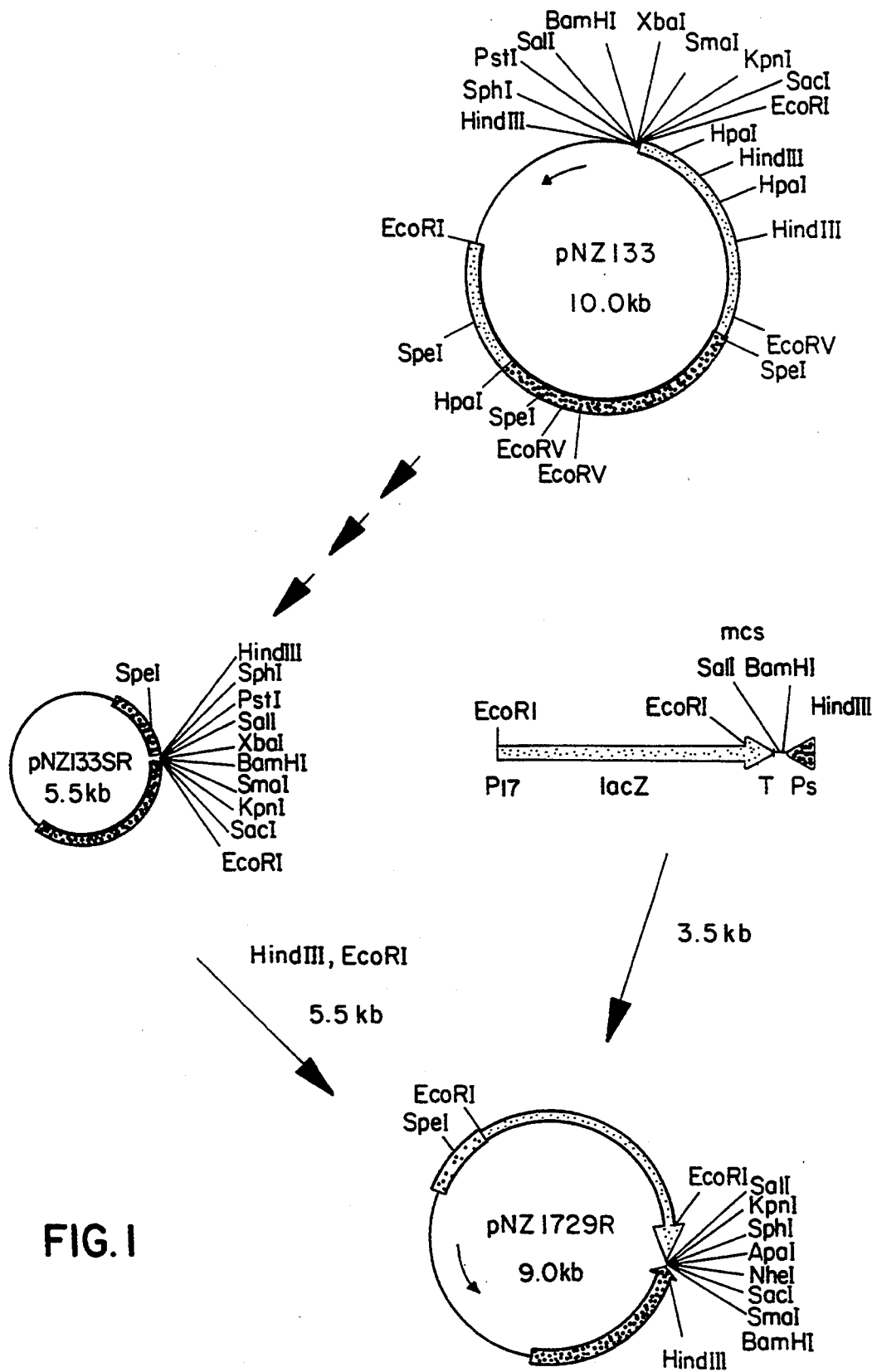
FIG. 1 shows the construction of insertion vector pNZ1729R.

The development of the recombinant FPV expressing the gBh gene of MDV and protecting the chickens against MD involved a multi-step procedure including: 1) construction of an insertion vector using a randomly-selected non-essential region of FPV DNA cloned into bacterial plasmid pUC18; 2) cloning and sequencing of the MDV gB homologue of HSV gB gene; 3) construction of a transfer vector including the gBh gene and the lacZ reporter gene in opposite directions and under the control of different poxvirus promoters; 4) transfection of FPV infected chicken embryo fibroblast (CEF) cultures with this transfer vector, generation of recombinants and purification of recombinants expressing the lacZ; 5) demonstration of expression of the MDV gBh antigen in CEF cultures infected with the recombinant FPV; and 6) demonstration of full protection offered by FPV recombinant vaccine against death and tumors caused by virulent tumorigenic MDV.

The insertion vector for use as the vehicle to transfer the gBh gene of MDV to FPV is pNZ1729R. This insertion vector was derived through multiple molecular manipulation of a cloned nonessential region of FPV DNA, Yanagida et al, European Patent Application Publication No. 0 284 416 (1988), and insertion of a lacZ bacterial gene as a reporter gene and creation of a multiple cloning site for insertion of foreign genes into this region of FPV DNA. A 3.0 kilobase (kb) pair fragment of FPV DNA was cloned into an appropriate cloning site of the bacterial plasmid pUC18. The resulting construct was altered by several restriction endonuclease (RE) digestions, religation and insertion of a multiple cloning site. The beta-galactosidase gene (lacZ) of *E. coli* was inserted into a unique RE site of this FPV DNA after having been linked to a poxvirus promoter followed by an initiation ATG codon and terminated with a transcriptional termination signal for poxvirus early promoter, Yuen et al, PNAS USA, 84:6417–6421 (1987). When this construct was transfected into FPV infected cells, recombinant viruses were generated that produced the product of the lacZ gene; the beta-galactosidase which in turn gave rise to blue plaques in the presence of the Blu-o-gal substrate.

In separate experiments the MDV gBh gene homologue of HSV gB gene was cloned into the bacterial plasmid pUC18. The nucleotide sequence of this gene was determined by analyzing a set of deletion mutants by the dideoxy chain termination reaction, Sanger et al, PNAS USA, 74:5463–5467 (1977). One of these mutants (pUCgBdB13), which was found to contain the entire coding region of MDVgBh, was used for construction of the transfer vector pNZ29RMDgB-S. Site specific mutagenesis, Tsurushita et al, Gene, 62:135–139 (1988) was used to change a potential poxvirus early transcription termination signal, Yuen et al, PNAS USA, 84:6417–6421 (1987), in the gBh gene of MDV without changing the amino acid of the translation product. In addition, a number of molecular procedures including RE digestion, ligation, site specific mutation, polymerase chain reaction (PCR) with appropriate primers were applied to properly insert the gBh gene of MDV from the mutant pUCgBdB13 into the pNZ1729R insertion vector to create the transfer vector, pNZ29RMDgB-S.

Purified pNZ29RMDgB-S plasmid was used to transfect CEF cultures infected with a large-plaque phenotype isolated from a vaccine FPV (CEVA strain) and the progeny virus released by these cells were assayed for recombinant virus producing blue plaques in the presence of Blu-o-gal. Recombinants were purified and tested for stability, structure of viral DNA, expression of lacZ and synthesis of gBh antigen of MDV in cell culture. Purified recombinants produced beta-galactosidase (blue plaques) and the gBh antigen as tested by immunofluorescence (IF) or immunoprecipitation assays using monoclonal antibody specific to MDV gBh antigen or convalescent serum from an MDV infected chicken. Three identical bands of 100 kd, 60 kd, and 49 kd in molecular weight were observed in extracts of cells infected with rec.FPV/MDVgBh and MDV. These polypeptides were also shown to be glycosylated. Similar glycoproteins were identified with the same monoclonal antibody in the MDV "B antigen complex" and were referred to as gP100, gP60, and gP49, Sithole et al, J. Virol., 62:4270–4279 (1988). Our finding is the first clear demonstration that MDV gBh gene codes for these three glycoproteins referred to as the "B antigen complex".

Three-week-old chickens were vaccinated with the recombinant FPV expressing the MDV gBh antigen and sera from these chickens were assayed for the presence of antibodies against MDV infected cells in culture. Positive antibodies to MDV gBh antigen were found in these sera indicating that the MDV gBh gene was efficiently expressed in the chicken and induced an immune response.

Separate groups of unvaccinated chickens were vaccinated at one day of age with parental FPV, recombinant FPV (rec.FPV) expressing MDV gBh antigen or a conventional MD vaccine (HVT). All groups were later challenged with tumorigenic GA isolate of MDV. Chickens vaccinated with rec.FPV as well as those vaccinated with HVT were fully protected against MD whereas the unvaccinated control chickens and those vaccinated with parental FPV died or had MD specific tumors.

Similar vaccination trials were performed to determine the effect of vaccine dose, route of vaccination, and promoter strength on immunity against MD and the ability of rec.FPV/MDVgBh to protect against very virulent strains of MDV. Chickens vaccinated with a dose of $10^4$ PFU of rec.FPV/MDVgBh were protected against challenge with three different strains of MDV tested. Vaccination route; intramuscular (IM) intraabdominal (IA) or vaccination by IM and IA did not seem to alter the level of protection as all chickens from each group were fully protected against MD. We generated another rec.FPV (rec.FPV/MDVgBh-P7.5) which expresses the MDVgBh gene under the control of vaccinia virus 7.5 kd protein gene promoter (P7.5), Ventakesan et al, Cell, 125:805–813 (1981) and tested its ability to protect against MD in comparison with the rec.FPV/MDVgBh which is driven by a poxvirus synthetic promoter (Ps). The rec.FPV/MDVgBh-P7.5 also gave a good protective immunity against MD but not as good as that obtained by vaccination with rec.FPV/MDVgBh driven by the poxvirus synthetic promoter. We also showed the ability of rec.FPV/MDVgBh to protect against two very virulent strains of MDV (RB1B; Schat et al, Avian Pathol., 11:593–605 (1982) and Md5; Witter et al, Avian Dis., 24:210–232 (1980)).

The cell-free vaccine of the present invention can be prepared by a variety of techniques. For example, a cell culture in which the recombinant virus of the present invention can grow and replicate is infected with the recombinant virus of the present invention. The cell culture is then incubated until the virus has had an opportunity to replicate in the cell culture. The cells are then harvested and disrupted. The cell debris can then be centrifuged to produce a pellet of cell debris at the bottom of the centrifuge tube and a substantially higher-titer cell-free supernatant containing the recombinant virus. The cell-free supernatant, which will consist primarily of the cell culture medium and the recombinant FPV, is then used as a vaccine containing the recombinant virus. In the alternative, the cell-free supernatant is lyophilized to produce a lyophilized vaccine which is reconstituted with a pharmaceutically acceptable carrier such as physiological saline prior to use.

The vaccine of the present invention can be administered to chickens in any manner which allows the recombinant virus in the vaccine to infect the chickens and produce a protective immune response. For example, the vaccine can be applied to the chickens subcutaneously (s.c.) by scratching the skin or injection with a needle or other implement which contains the virus. The recombinant virus can also be dissolved or suspended in the drinking water of chickens for oral administration. The virus may also be mixed with a solid carrier (e.g. chicken feed) for oral administration. Other modes of administration are also contemplated such as inhalation by use of an aerosol or spray, intravenous administration, intramuscular administration, intraperitoneal administration, wing web administration, etc.

A preferred dose for injection appears to be $10^4$ plaque forming units (PFU) per chicken in 0.1 ml of a physiologically acceptable liquid carrier. Thus, the injectable solution will contain $10^5$ PFU/ml of carrier, usually between $10^4$ to $10^6$ PFU/ml of carrier. The dose and route of administration should be selected to elicit a protective immune response.

The recombinant virus of the present invention can contain a gene encoding more than one antigen such as one or more antigens selected from the group consisting of glycoprotein B homologue, glycoprotein C homologue, glycoprotein D homologue, glycoprotein H homologue and tegument proteins. In the alternative, multiple recombinant viruses can be included in the vaccine wherein each individual virus expresses a single gene. It is believed that by exposing the chickens to multiple antigens of the Marek's Disease Virus which elicit a protective immune response, improved protection may be achieved.

In addition to the specific glycoproteins mentioned above, it is also contemplated in accordance with the present invention that fragments of the genes coding for the above-mentioned antigens or variants of the genes which code for variants of the above-mentioned antigens may also be useful as long as the resulting protein (antigen) elicits a protective immune response. It is contemplated that such fragments or variants would code for proteins (antigens) which have substantially the same amino acid sequence as the natural proteins to thereby elicit a substantially equivalent immune response in the host. The fragments or variants will usually encode a protein which has more than 80%, preferably more than 90%, and more preferably more than 95% homology to the natural protein.

The recombinant virus of the present invention has the gene for the antigen inserted into the virus under control of appropriate promoters, terminators, etc. so that the virus, after it infects a host cell, can express the protein (antigen) thereby eliciting an immune response in the host. Ps, which is a strong synthetic poxvirus promoter which produces high levels of expression during both the early and late stages of infection, is particularly useful. Promoter P7.5 is also useful. Other poxvirus promoters may also be used.

EXAMPLE 1

Construction of Insertion Vector pNZ1729R (FIG. 1)

A 3.0 kb HpaI-SpeI fragment from a 7.3 kb EcoRI fragment of FPV NP strain, Yanagida et al, European Patent Application No. 0 284 416 (1988), was subcloned into pUC18 in several steps in a conventional manner. After eliminating all multiple cloning sites from both junction regions between pUC18 and FPV DNA, a multiple cloning site (HindIII-EcoRI 52 bp from pUC18) was inserted into two adjacent EcoRV sites in the cloned FPV fragment with linkers (HindIII linker; 5'-CAAGCTTG-3', EcoRI linker; 5'-GGAATTCC-3') to make pNZ133SR.

A 3.5 kb EcoRI-HindIII fragment (shown in FIG. 1 right center) was derived by ligating-annealing oligos 1 (SEQ. ID. NO. 1) and 2 (SEQ. ID. NO. 2) (FIG. 2; containing a fowlpox promoter followed by an ATG codon for lacZ), to lacZ gene (from pMC1871 and pMA001), Shirakawa et al, Gene, 28:127–132 (1984) and annealing oligos 3 (SEQ. ID. NO. 3), 4 (SEQ. ID. NO. 4), 5 (SEQ. ID. NO. 5), 6 (SEQ. ID. NO. 6), 7 (SEQ. ID. NO. 7), 8 (SEQ. ID. NO. 8), 9 (SEQ. ID. NO. 9) and 10 (SEQ. ID. NO. 10) (FIG. 2; containing synthetic poxvirus promoter, followed by a multiple cloning site and a two directional poxvirus early transcriptional termination signal (SEQ. ID. NO. 11), Yuen et al, PNAS, 88:6417–6421 (1989)). The 3.5 kb EcoRI-HindIII fragment was inserted in pNZ133SR to make the pNZ1729R insertion vector.

EXAMPLE 2

Figure 3:
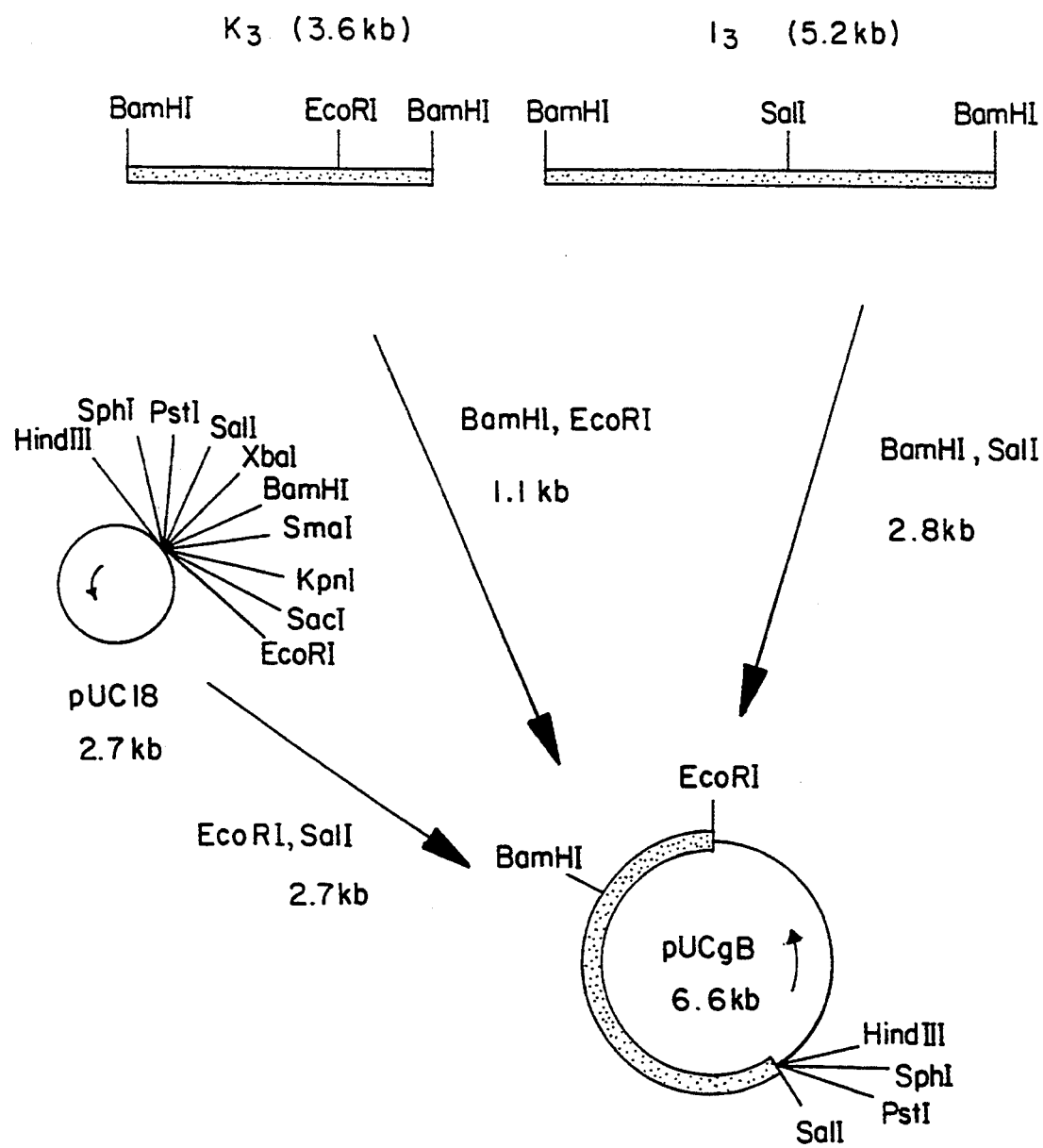
FIG. 3 shows the steps taken to clone MDV gBh of HSV gene.

Cloning of MDV gBh Gene (FIG. 3)

The MDV gBh of HSV from a BamHI I3 (5.2 kb) and K3 (3.6 kb) fragment of MDV GA strain was cloned into pUC18 plasmid. A 2.8 kb BamHI-SalI subfragment from I3 fragment and a 1.1 kb BamHI-EcoRI subfragment from K3 fragment were ligated with EcoRI, SalI digested pUC18.

The overall sequence of the putative MDV gBh was determined by sequencing a set of deletion mutants by the Sanger dideoxy chain termination method, Sanger et al, PNAS USA, 74:5463–5467 (1977). The nucleotide and amino acid sequences (SEQ. ID. NOS. 12 and 13) were found to be identical with the published sequences of the gBh of RB1B strain of MDV, Ross et al, J. Gen. Virol., 70:1789–1804 (1988).

EXAMPLE 3

Figure 4:
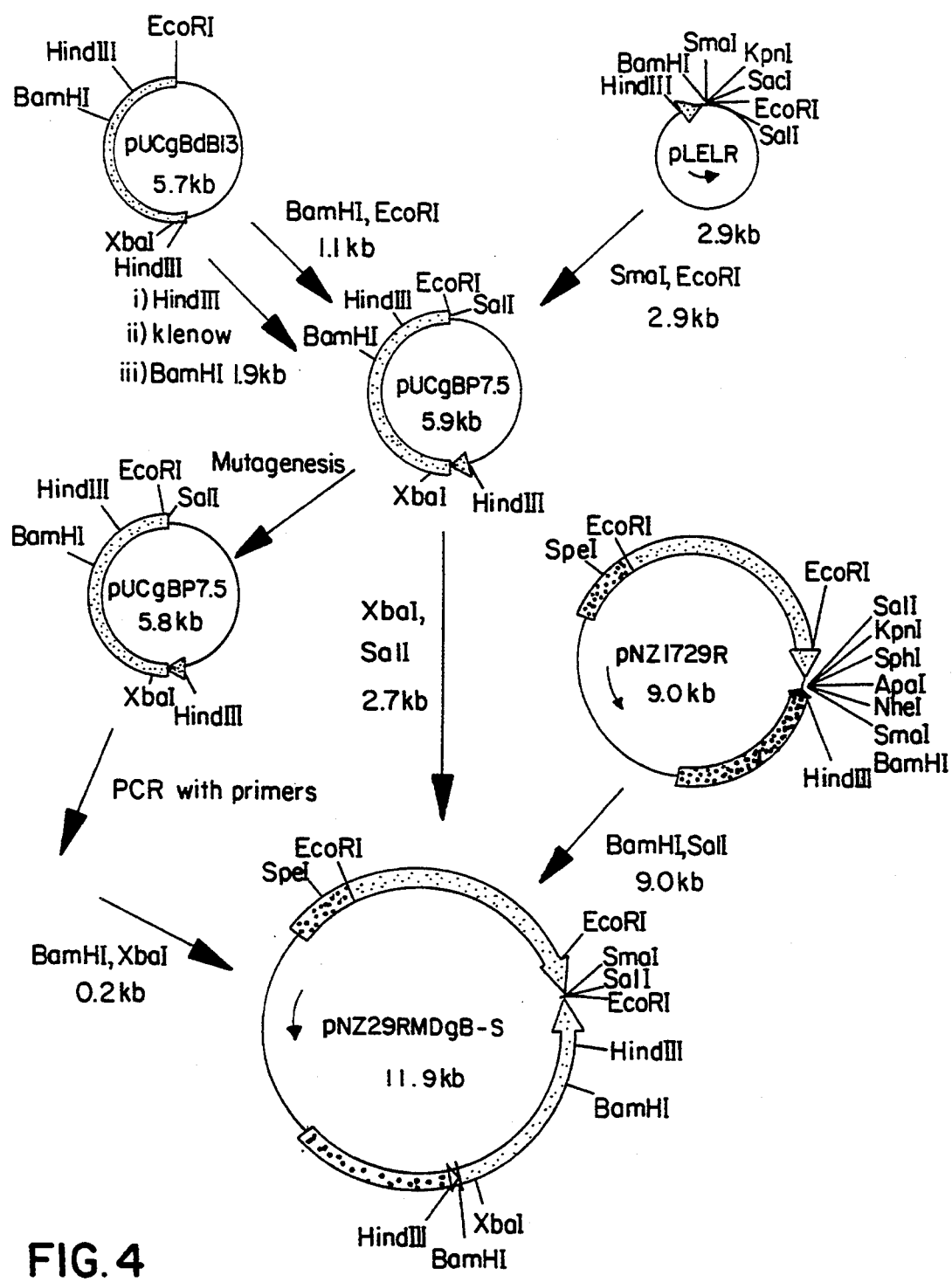
FIG. 4 shows the construction of transfer vector pNZ29RMDgB-S.

Construction of Transfer Vector pNZ29RMDgB-S (FIG. 4)

One of the deletion mutants for sequencing the MDV gBh gene, named pUCgBdB13, that contained the entire coding region of the gBh with about 250 bp 5′ flanking region was chosen for insertion into insertion vector pNZ1729R.

The plasmid pLELR, which was derived from pNZ1037, Ogawa et al, Vaccine, 8:488–490 (1990), with synthetic adapter

5′-CGAATTCGTCGAC-3′ (SEQ. ID. NO. 14)

3′-TCGAGCTTAAGCAGCTGTTAA-5′ (SEQ. ID. NO. 15)

to make a SalI site next to EcoRI site, was digested with SmaI and EcoRI and was ligated with a 1.9 kb HindIII (Klenow-blunt)-BamHI fragment and a 1.1 kb BamHI-EcoRI fragment, both from pUCgB-dB13. Site specific mutagenesis was used to eliminate about 250 bp 5′ flanking region and to change a potential poxvirus early transcription termination signal in the gBh gene of pUCgB7.5 (TTTTTTT; nucleotides 382–388 in SEQ. ID. NO. 12) to TATTTTT. Oligonucleotides for site specific mutagenesis of(P7.5-gB) 34mer; was oligonucleotide (SEQ. ID. NO. 16) for site-specific mutagenesis of (TTTTTTT) 26mer; was (SEQ. ID. NO. 17).

In order to create a new BamHI site in front of translation initiation codon (ATG) of gBh for connecting the gBh gene with a synthetic promoter, PCR was performed with synthetic oligonucleotides (SEQ. ID. NO. 18) and (SEQ. ID. NO. 19).

About 200 bp BamHI-XbaI fragment from the PCR product was ligated with a 2.7kb XbaI-SalI fragment of gBh and BamHI, SalI digested vector pNZ1729R to make transfer vector pNZ29RMDgB-S.

EXAMPLE 4

Generation and Purification of Recombinant FPV/MDVgBh

CEF cultures propagated as monolayers were infected with 0.1 multiplicity of infection (moi) of a large-plaque phenotype virus isolated from a vaccine preparation of FPV. Three hours after infection, cells were dispersed by trypsinization and brought into suspension. $2 \times 10^7$ cells from this suspension were mixed with 10 micrograms (μg) of transfer vector pNZ29RMDgB-S in a Cell Porator (Bethesda Research Laboratories, Inc., Bethesda, Md.) according to the manufacturer's specifications. The mixture of cell suspension and the transfer vector DNA in 0.8 ml of Saline G containing 0.14M NaCl, 0.5 mM KCl, 1.1 mM $Na_2HPO_4.12 H_2O$, 1.5 mM $KH_2PO_4$, 0.5mM $MgCl_2.6H_2O$, and 0,011% glucose was subjected to electropotation under an electric field of 300 $V \times cm^{-1}$ at room temperature using 330 μF of capacitance. Transfected cells were then incubated at 37° C. for 72 hours (h) and were then lysed by three cycles of freezing and thawing. The released virus was screened for recombinants as follows.

Secondary CEF cultures were infected with serial ten-fold dilutions of the progeny virus from lysates and overlayed with 10 ml of agar solution containing growth medium and allowed to harden at room temperature and incubated at 37° C. until typical FPV plaques appeared. Another agar overlay containing 250 μg/ml of Blu-o-gal (BRL) was added to each plate and incubated at 37° C. for another 48 h. Blue plaques appeared at a rate of approximately 1% of the total progeny virus. These blue plaques were removed from agar and the recombinant virus released from this agar was further purified in the same manner until all FPV plaques produced blue plaques when assayed in the presence of Blu-o-gal. This process usually took only three passages. The purified recombinant virus was named rec.FPV/MDVgBh. The DNA from this rec.FPV/MDVgBh was analyzed by Southern blot hybridization and found to contain the MDVgBh and lacZ genes at the expected positions. The virus rec.FPV/MDVgBh was deposited at the American Type Culture Collection (12301 Parklawn Drive, Rockville, Md., U.S.A.) on Jun. 20, 1991 and was assigned deposit number ATCC-VR-2330 under the conditions of the Budapest Treaty.

EXAMPLE 5

Expression of MDV gBh Antigen in Cell Culture

In order to show that rec.FPV/MDVgBh synthesizes the gBh antigen, CEF cultures infected with this virus were examined by IF using antibodies specifically raised against this antigen. CEF cultures infected with rec.FPV/MDVgBh were incubated at 37° C. until typical FPV plaques were developed. These cultures were fixed in cold acetone, then reacted with appropriate dilutions of convalescent chicken serum against the GA strain of MDV or a monoclonal antibody specific to MDV gB antigen, Silva et al, Virology, 136:307–320 (1984). These cultures were then reacted with fluorescein conjugated anti-chicken or anti-mouse immunoglobulins, respectively, and after thorough washing to remove non-specific staining they were examined with a microscope under ultraviolet (UV) illumination. CEF cultures infected with non-recombinant parental FPV were similarly stained. Specific cytoplasmic staining of cells was observed in cultures infected with the rec.FPV/MDVgBh and not in cultures infected with the non-recombinant parental FPV. These observations clearly showed that the recombinant virus was capable of synthesizing the product of gBh gene of MDV in cell cultures.

Figure 5:
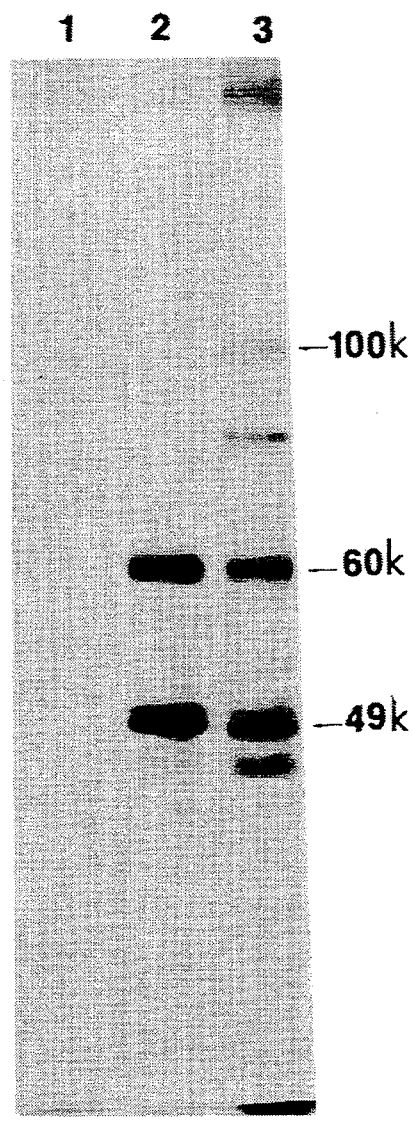
FIG. 5 shows the immunoprecipitation of cells infected with rec.FPV/MDVgBh or with GA strain of MDV.

Western blot analysis of proteins from recombinant FPV-infected cells did not reveal the expected glycoprotein bands associated with gBh gene when lysates were boiled in buffer as in normal conditions of the assay. However, when solubilized with sample buffer at room temperature instead of 100° C. a high molecular weight band was detected with a Rf value similar to that in MDV infected cell lysates solubilized at room temperature. In order to clearly show the three species of glycoproteins previously shown to be associated with MDV "B antigen complex", we examined the expression of the gBh gene by immunoprecipitation as described by Silva et al, Virology, 136:307–320 (1984). Secondary CEF cultures infected with either parental or recombinant FPV at an moi of 15 were incubated at 37° C. for 4 hours. Then, the medium was replaced with 1 ml of fresh Methionine-free medium and incubated for another hour. About 40 uCi of $^{35}S$-Methionine (NEN, Wilmington, Del.) was then added and the cultures were incubated for an additional 12 hours. Cells were washed twice in PBS, scraped, and transferred to a 15 ml Falcon tube. Cells were centrifuged, resuspended in lysis buffer (150 mM NaCl, 1% sodium deoxycholate, 1% Triton X-100, 0.1% SDS, and 10 mM Tris HCl, pH 7.5) and incubated at room temperature for 30 minutes. One half volume of 10% (v/v) *S. aureus* Cowan 1 (SAC) was added to cell lysate, and incubated for 30 minutes on ice. The lysate was then centrifuged and the supernatant was collected. About 3 μl of monoclonal antibody, IAN86 against MDV "B antigen complex", Silva et al, Virology, 136:307-320 (1984), was added to 100 μl of lysate and incubated for 30 minutes on ice. An equal volume of 10% (v/v) SAC was added and incubated on ice for 30 minutes. Immunoprecipitates were then washed, suspended in sample buffer, and then boiled. After centrifugation, supernatant was analyzed by sodium dodecyl sulphate-polyacrylamide gel electrophoresis, Laemmli, Nature, 207:680-685 (1970). FIG. 5 shows the result of immunoprecipitation with a monoclonal antibody (IAN86) specific to the MDV "B antigen complex". Lane 1 is a control containing non-recombinant fowlpox virus cell lysate. Three identical bands of 100 kd, 60 kd and 49 kd in molecular weight were observed in extracts of cells infected with rec.FPV/MDVgBh (FIG. 5, lane 2) and MDV (FIG. 5, lane 3). These glycoproteins were also shown to be glycosylated by demonstrating that they uptake radioactively labelled glucosamine. Similar glycoproteins were identified with the same monoclonal antibody in the MDV "B antigen complex" and were referred to as gP100, gP60, and gP49, Sithole et al, J. Virol., 62:4270-4279 (1988).

This is the first clear demonstration that MDV gBh gene codes for these three glycoproteins previously referred to as the "B antigen complex". The latter two glycoproteins are believed to be the cleavage products of gP100 which may explain the rather weak signals obtained for this glycoprotein in our immunoprecipitation of cell lysates from late stages of infection (FIG. 5).

EXAMPLE 6

Ability of the rec.FPV/MDVgBh to Induce Humoral Immunity Against MDV gBh Antigen in Chickens A group of five, 3-week-old specific pathogen free (SPF) line O chickens raised in this laboratory were injected with $10^6$ infectious doses (PFUs) of rec.FPV/MDVgBh intramuscularly while another group of five similar chickens were injected with the non-recombinant FPV. Similar booster inoculations were given after 2 and 4 weeks. Sera were collected from all chickens two weeks after the last inoculation. Sera were tested for the presence of antibodies to MDV gBh antigen. Coverslip monolayer cultures of CEF were infected with MDV GA strain and incubated at 37° C. until typical MDV plaques were visible with the light microscope. These cultures were then reacted with appropriate dilutions of sera from chickens of both groups followed by extensive washing and reaction with fluorescein conjugated goat anti-chicken immunoglobulin. Cultures were then examined by a microscope equipped with an UV illuminator. Sera from chickens immunized with rec.FPV/MDVgBh reacted positively with MDV infected cells and stained cytoplasmic antigens typical of gBh antigen of MDV. Sera from chickens immunized with the non-recombinant FPV failed to stain the gBh antigen of MDV. These results demonstrated clearly that the rec.FPV/MDVgBh is capable of inducing specific antibodies against the gBh antigen of MDV when injected into chickens.

EXAMPLE 7 rec.FPV/MDVgBh Fully Protects Chickens Against Challenge with Virulent Tumor Inducing MDV Separate groups of 1-day-old chicks from 15×7 chicken line susceptible to MD were vaccinated with $10^6$ plaque forming units (PFU) of rec.FPV/MDVgBh, $10^6$ PFU of parental FPV or $10^3$ PFU of HVT vaccine. Another group of similar chicks was kept unvaccinated. All were kept in strict isolation. At 12 days of age all were challenged with $1 \times 10^3$ PFU of virulent tumor causing GA strain of MDV. A fifth group of chickens were neither vaccinated nor challenged. Mortality caused by MD was recorded during the trial and at the end of the 10 week trial all chickens were examined for gross lesions and tumors typical of MD. The results of this study are presented in Table 1.

In a second trial one-day-old chicks were either vaccinated intraabdominally (IA) with $10^3$ PFU of HVT or vaccinated with $10^4$ PFU of rec.FPV/MDVgBh half intra-muscularly (IM) and half IA. One group received the vaccine only IA and another group received the vaccine IM. One group received rec.FPV/MDVgBh-P7.5 in which the MDVgBh gene is driven by the vaccinia virus 7.5 kd protein promoter (P7.5). At six days post vaccination, six groups were challenged with $10^3$ PFU of pathogenic GA strain of MDV while three other groups each were challenged with $10^3$ PFU of very virulent strains of MDV (RB1B strain, Schat et al, Avian Pathol., 11:593-605 (1982) or Md5, Witter et al, Avian Dis., 24:210-232 (1980)). The results of this study are presented in Table 2.

TABLE 1

| Protection against MD by rec.FPV/MDVgBh. | | | | |
|---|---|---|---|---|
| Lot. | Vaccine | Challenge | MD mortality | MD gross lesions | % MD |
| 1 | None | GA-MDV | 9/15 | 1/6 | 66 |
| 2 | HVT | GA-MDV | 0/15 | 0/15 | 0 |
| 3 | rec.FPV/ MDVgBh | GA-MDV | 0/15 | 0/15 | 0 |
| 4 | parental FPV | GA-MDV | 3/15 | 3/12 | 40 |
| 5 | None | None | 0/10 | 0/10 | 0 |

TABLE 2

| Protection against different strains of MDV by rec.FPV/MDVgBh. | | | | | |
|---|---|---|---|---|---|
| Lot. | Vaccine | Vaccine route | MDV challenge strain | MD mortality | MD gross lesions | % MD |
| 1 | None | | GA | 8/10 | 1/2 | 90 |
| 2 | HVT | IA | GA | 0/10 | 0/10 | 0 |
| 3 | rec.FPV/ MDVgBh | IA&IM | GA | 0/10 | 0/10 | 0 |
| 4 | rec.FPV/ MDVgBh-P7.5 | IA&IM | GA | 1/10 | 1/9 | 20 |
| 5 | rec.FPV/ MDVgBh | IA | GA | 0/10 | 0/10 | 0 |
| 6 | rec.FPV/ MDVgBh | IM | GA | 0/10 | 0/10 | 0 |
| 7 | None | | Md5 | 8/10 | 2/2 | 100 |
| 8 | rec.FPV/ MDVgBh | IA&IM | Md5 | 0/10 | 0/10 | 0 |
| 9 | HVT | IA | Md5 | 0/10 | 0/10 | 0 |
| 10 | None | | RB1B | 9/10 | 0/1 | 90 |
| 11 | rec.FPV/ MDVgBh | IA&IM | RB1B | 0/10 | 1/10 | 10 |
| 12 | HVT | IA | RB1B | 1/10 | 0/9 | 10 |

TABLE 2-continued

Protection against different strains of MDV by rec.FPV/MDVgBh.

| Lot. | Vaccine | Vaccine route | MDV challenge strain | MD mortality | MD gross lesions | % MD |
|------|---------|---------------|----------------------|--------------|------------------|------|
| 13   | None    |               | None                 | 0/5          | 0/5              | 0    |

A significant number of unvaccinated chickens in groups challenged with all three strains died of MD or had MD specific tumors and lesions at the end of the trial. Those vaccinated with rec.FPV/MDVgBh or HVT were fully protected against the GA and the very virulent Md5 strains. Those vaccinated with either of the above vaccines were also significantly and equally protected against the very virulent RB1B strains of MDV. There was no significant difference between the level of protection induced by vaccination route as all birds vaccinated IM, IA or IM&IA and challenged with the GA strain of MDV were fully protected against MD. The rec.FPV/MDVgBh which expresses the MDVgBh gene under the control of a poxvirus synthetic promoter was superior to the rec.FPV/MDVgBh-P7.5 which expresses the same gene under the control of vaccinia virus P7.5 promoter in that it fully protected against MD while the latter recombinant did offer a significant protection but not as well as the recombinant driven by the poxvirus synthetic promoter.

A significant number of unvaccinated chickens and those vaccinated with parental FPV that were challenged with MDV died of MD or had MD lesions and tumors at the end of trial. Chickens vaccinated with rec.FPV/MDVgBh were fully protected against MD with no mortality and no lesions typical of MD. Similarly, all chickens vaccinated with HVT were protected. No mortality or lesions were present in chickens that were not injected with MDV. These results showed that the rec.FPV/MDVgBh fully protected chickens against MD, just as well as the widely used commercial HVT vaccine.

EXAMPLE 8

Preparation of Cell Free Vaccine from Recombinant FPV/MDVgBh

Confluent monolayers of chicken embryo fibroblast cultures containing about $4 \times 10^7$ cells in plastic tissue culture dishes are infected with 1 ml of rec.FPV/MDVgBh stock containing approximately $1 \times 10^6$ PFU of the virus and allowed to incubate at 37° C. for 2 hours. At this time, 20 ml of fresh culture medium is added to each plate. Cultures then incubated in a 5% $CO_2$ incubator at 37° C. for 3 to 4 days until the entire monolayer of cells shows signs of infection. At this time, cell monolayer is scraped off from the culture dish using a cell lifter (Costar Corp.). Cells are then pelleted by centrifugation and suspended in 5 ml of the original culture medium and sonicated at half strength on ice for 60 seconds using a Braun-Sonic U sonicator (Braun Co. Ltd.). Sonicated material is then centrifuged to remove cell debris and the supernatant fluid is added to the remainder of the original culture medium. This vaccine preparation is then dispensed in 1 ml aliquots, placed in glass vials and stored at −70° C. in a freezer.

What is claimed is:

1. The recombinant fowlpox virus rec.FPV/MDVgBh and which is assigned deposit number ATCC VR-2330.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATTCGAGCT CGGATCGTTG AAAAAATAAT ATAGATCCTA AAATGGAA    48

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GATCTTCCAT TTAGGATCT ATATTATTTT TTCAACGATC CGAGCTCG    48

( 2 ) INFORMATION FOR SEQ ID NO:3:

( i ) SEQUENCE CHARACTERISTICS:
        ( A ) LENGTH: 55 base pairs
        ( B ) TYPE: nucleic acid ( C ) STRANDEDNESS: single
( D ) TOPOLOGY: linear ( x i ) SEQUENCE DESCRIPTION: SEQ ID NO:3:

AGCTTTTTTT TTTTTTTTT TTTGGCATAT AAATAATAAA TACAATAATT AATTA     55

( 2 ) INFORMATION FOR SEQ ID NO:4:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CGCGTAATTA ATTATTGTAT TTATTATTTA TATGCCAAAA AAAAAAAAA AAAAA     55

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CGCGTAAAAA TTGAAAAACT ATTCTAATTT ATTGCACTCG     40

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATCCGAGTG CAATAAATTA GAATAGTTTT TCAATTTTTA     40

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATCCCCGGG CGAGCTCGCT AGCGGGCCCG CATGCGGTAC CG     42

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCGACGGATC CGCATGCGGG CCCGCTAGCG AGCTCGCCCG GG     42

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
TCGACCCGGT ACATTTTTAT AAAAATGTAC CCGGGGATC                    39
```

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GATCCCCGGG TACATTTTTA TAAAAATGTA CCGGG                        35
```

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
ATTTTTATAA AAAT                                               14
```

( 2 ) INFORMATION FOR SEQ ID NO:12:

( i ) SEQUENCE CHARACTERISTICS:
        ( A ) LENGTH: 3209 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 357..2951

( x i ) SEQUENCE DESCRIPTION: SEQ ID NO:12:

```
ATTTAAATGT GGCGAATTGC ACATCTGTCG TGCCGACAGT TTGCAGATCA ACAGCAATGG     60

AGACTATGTA TGGAAAAATG GAATATATAT AACATATGAA ACCGAATATC CACTTATAAT   120

GATTCTGGGG TCAGAATCAA GCACTTCAGA AACGCAAAAT ATGACTGCAA TTATTGATAC   180

AGATTTTTTT CGTTGCTTTA TTCTATTTTG CAGTATATGG CCCCCGTTAC GGCAGATCAG   240

GTGCGAGTAG AACAGATTAC CAACAGCCAC GCCCCCATCT GACCCGTCCA ATATTCTTGT   300

GTCCCTGCAT TTTATCTCAC ACAATTTATG AACAGCATCA TTAAGATCAT CTCACT       356

ATG CAC TAT TTT AGG CGG AAT TGC ATT TTT TTC CTT ATA GTT ATT CTA     404
Met His Tyr Phe Arg Arg Asn Cys Ile Phe Phe Leu Ile Val Ile Leu
  1               5                  10                  15

TAT GGT ACG AAC TCA TCT CCG AGT ACC CAA AAT GTG ACA TCA AGA GAA     452
Tyr Gly Thr Asn Ser Ser Pro Ser Thr Gln Asn Val Thr Ser Arg Glu
             20                  25                  30

GTT GTT TCG AGC GTC CAG TTG TCT GAG GAA GAG TCT ACG TTT TAT CTT     500
Val Val Ser Ser Val Gln Leu Ser Glu Glu Glu Ser Thr Phe Tyr Leu
         35                  40                  45

TGT CCC CCA CCA GTG GGT TCA ACC GTG ATC CGT CTA GAA CCG CCG CGA     548
Cys Pro Pro Pro Val Gly Ser Thr Val Ile Arg Leu Glu Pro Pro Arg
     50                  55                  60

AAA TGT CCC GAA CCT AGA AAA GCC ACC GAG TGG GGT GAA GGA ATC GCG     596
Lys Cys Pro Glu Pro Arg Lys Ala Thr Glu Trp Gly Glu Gly Ile Ala
 65                  70                  75                  80

ATA TTA TTT AAA GAG AAT ATC AGT CCA TAT AAA TTT AAA GTG ACG CTT    644
 Ile Leu Phe Lys Glu Asn Ile Ser Pro Tyr Lys Phe Lys Val Thr Leu
                 85                  90                  95

TAT TAT AAA AAT ATC ATT CAG ACG ACG ACA TGG ACG GGG ACG ACA TAT     692
Tyr Tyr Lys Asn Ile Ile Gln Thr Thr Thr Trp Thr Gly Thr Thr Tyr
```

|       |       |       |       |       | 100   |       |       |       |       | 105   |       |       |       |       | 110   |       |       |      |
|-------|-------|-------|-------|-------|-------|-------|-------|-------|-------|-------|-------|-------|-------|-------|-------|-------|-------|------|
| AGA   | CAG   | ATC   | ACT   | AAT   | CGA   | TAT   | ACA   | GAT   | AGG   | ACG   | CCC   | GTT   | TCC   | ATT   | GAA   |       |       | 740  |
| Arg   | Gln   | Ile   | Thr   | Asn   | Arg   | Tyr   | Thr   | Asp   | Arg   | Thr   | Pro   | Val   | Ser   | Ile   | Glu   |       |       |      |
|       |       | 115   |       |       |       |       | 120   |       |       |       |       | 125   |       |       |       |       |       |      |

| GAG | ATC | ACG | GAT | CTA | ATC | GAC | GGC | AAA | GGA | AGA | TGC | TCA | TCT | AAA | GCA | 788 |
|-----|-----|-----|-----|-----|-----|-----|-----|-----|-----|-----|-----|-----|-----|-----|-----|-----|
| Glu | Ile | Thr | Asp | Leu | Ile | Asp | Gly | Lys | Gly | Arg | Cys | Ser | Ser | Lys | Ala |     |
|     |     | 130 |     |     |     |     | 135 |     |     |     |     | 140 |     |     |     |     |

| AGA | TAC | CTT | AGA | AAC | AAT | GTA | TAT | GTT | GAA | GCG | TTT | GAC | AGG | GAT | GCG | 836 |
|-----|-----|-----|-----|-----|-----|-----|-----|-----|-----|-----|-----|-----|-----|-----|-----|-----|
| Arg | Tyr | Leu | Arg | Asn | Asn | Val | Tyr | Val | Glu | Ala | Phe | Asp | Arg | Asp | Ala |     |
| 145 |     |     |     |     | 150 |     |     |     |     | 155 |     |     |     |     | 160 |     |

| GGA | GAA | AAA | CAA | GTA | CTT | CTA | AAA | CCA | TCA | AAA | TTC | AAC | ACG | CCC | GAA | 884 |
|-----|-----|-----|-----|-----|-----|-----|-----|-----|-----|-----|-----|-----|-----|-----|-----|-----|
| Gly | Glu | Lys | Gln | Val | Leu | Leu | Lys | Pro | Ser | Lys | Phe | Asn | Thr | Pro | Glu |     |
|     |     |     |     | 165 |     |     |     |     | 170 |     |     |     |     | 175 |     |     |

| TCT | AGG | GCA | TGG | CAC | ACG | ACT | AAT | GAG | ACG | TAT | ACC | GTG | TGG | GGA | TCA | 932 |
|-----|-----|-----|-----|-----|-----|-----|-----|-----|-----|-----|-----|-----|-----|-----|-----|-----|
| Ser | Arg | Ala | Trp | His | Thr | Thr | Asn | Glu | Thr | Tyr | Thr | Val | Trp | Gly | Ser |     |
|     |     |     |     | 180 |     |     |     |     | 185 |     |     |     |     | 190 |     |     |

| CCA | TGG | ATA | TAT | CGA | ACG | GGA | ACC | TCC | GTC | AAT | TGT | ATA | GTA | GAG | GAA | 980 |
|-----|-----|-----|-----|-----|-----|-----|-----|-----|-----|-----|-----|-----|-----|-----|-----|-----|
| Pro | Trp | Ile | Tyr | Arg | Thr | Gly | Thr | Ser | Val | Asn | Cys | Ile | Val | Glu | Glu |     |
|     |     |     | 195 |     |     |     |     | 200 |     |     |     |     | 205 |     |     |     |

| ATG | GAT | GCC | CGC | TCT | GTG | TTT | CCG | TAT | TCA | TAT | TTT | GCA | ATG | GCC | AAT | 1028 |
|-----|-----|-----|-----|-----|-----|-----|-----|-----|-----|-----|-----|-----|-----|-----|-----|------|
| Met | Asp | Ala | Arg | Ser | Val | Phe | Pro | Tyr | Ser | Tyr | Phe | Ala | Met | Ala | Asn |      |
|     | 210 |     |     |     |     | 215 |     |     |     |     | 220 |     |     |     |     |      |

| GGC | GAC | ATC | GCG | AAC | ATA | TCT | CCA | TTT | TAT | GGT | CTA | TCC | CCA | CCA | GAG | 1076 |
|-----|-----|-----|-----|-----|-----|-----|-----|-----|-----|-----|-----|-----|-----|-----|-----|------|
| Gly | Asp | Ile | Ala | Asn | Ile | Ser | Pro | Phe | Tyr | Gly | Leu | Ser | Pro | Pro | Glu |      |
| 225 |     |     |     |     | 230 |     |     |     |     | 235 |     |     |     |     | 240 |      |

| GCT | GCC | GCA | GAA | CCC | ATG | GGA | TAT | CCC | CAG | GAT | AAT | TTC | AAA | CAA | CTA | 1124 |
|-----|-----|-----|-----|-----|-----|-----|-----|-----|-----|-----|-----|-----|-----|-----|-----|------|
| Ala | Ala | Ala | Glu | Pro | Met | Gly | Tyr | Pro | Gln | Asp | Asn | Phe | Lys | Gln | Leu |      |
|     |     |     |     | 245 |     |     |     |     | 250 |     |     |     |     | 255 |     |      |

| GAT | AGC | TAT | TTT | TCA | ATG | GAT | TTG | GAC | AAG | CGT | CGA | AAA | GCA | AGC | CTT | 1172 |
|-----|-----|-----|-----|-----|-----|-----|-----|-----|-----|-----|-----|-----|-----|-----|-----|------|
| Asp | Ser | Tyr | Phe | Ser | Met | Asp | Leu | Asp | Lys | Arg | Arg | Lys | Ala | Ser | Leu |      |
|     |     |     | 260 |     |     |     |     | 265 |     |     |     |     | 270 |     |     |      |

| CCA | GTC | AAG | CGT | AAC | TTT | CTC | ATC | ACA | TCA | CAC | TTC | ACA | GTT | GGG | TGG | 1220 |
|-----|-----|-----|-----|-----|-----|-----|-----|-----|-----|-----|-----|-----|-----|-----|-----|------|
| Pro | Val | Lys | Arg | Asn | Phe | Leu | Ile | Thr | Ser | His | Phe | Thr | Val | Gly | Trp |      |
|     |     | 275 |     |     |     |     | 280 |     |     |     |     | 285 |     |     |     |      |

| GAC | TGG | GCT | CCA | AAA | ACT | ACT | CGT | GTA | TGT | TCA | ATG | ACT | AAG | TGG | AAA | 1268 |
|-----|-----|-----|-----|-----|-----|-----|-----|-----|-----|-----|-----|-----|-----|-----|-----|------|
| Asp | Trp | Ala | Pro | Lys | Thr | Thr | Arg | Val | Cys | Ser | Met | Thr | Lys | Trp | Lys |      |
|     | 290 |     |     |     |     | 295 |     |     |     |     | 300 |     |     |     |     |      |

| GAG | GTG | ACT | GAA | ATG | TTG | CGT | GCA | ACA | GTT | AAT | GGG | AGA | TAC | AGA | TTT | 1316 |
|-----|-----|-----|-----|-----|-----|-----|-----|-----|-----|-----|-----|-----|-----|-----|-----|------|
| Glu | Val | Thr | Glu | Met | Leu | Arg | Ala | Thr | Val | Asn | Gly | Arg | Tyr | Arg | Phe |      |
| 305 |     |     |     |     | 310 |     |     |     |     | 315 |     |     |     |     | 320 |      |

| ATG | GCC | CGT | GAA | CTT | TCG | GCA | ACG | TTT | ATC | AGT | AAT | ACG | ACT | GAG | TTT | 1364 |
|-----|-----|-----|-----|-----|-----|-----|-----|-----|-----|-----|-----|-----|-----|-----|-----|------|
| Met | Ala | Arg | Glu | Leu | Ser | Ala | Thr | Phe | Ile | Ser | Asn | Thr | Thr | Glu | Phe |      |
|     |     |     |     | 325 |     |     |     |     | 330 |     |     |     |     | 335 |     |      |

| GAT | CCA | AAT | CGC | ATC | ATA | TTA | GGA | CAA | TGT | ATT | AAA | CGC | GAG | GCA | GAA | 1412 |
|-----|-----|-----|-----|-----|-----|-----|-----|-----|-----|-----|-----|-----|-----|-----|-----|------|
| Asp | Pro | Asn | Arg | Ile | Ile | Leu | Gly | Gln | Cys | Ile | Lys | Arg | Glu | Ala | Glu |      |
|     |     |     | 340 |     |     |     |     | 345 |     |     |     |     | 350 |     |     |      |

| GCA | GCA | ATC | GAG | CAG | ATA | TTT | AGG | ACA | AAA | TAT | AAT | GAC | AGT | CAC | GTC | 1460 |
|-----|-----|-----|-----|-----|-----|-----|-----|-----|-----|-----|-----|-----|-----|-----|-----|------|
| Ala | Ala | Ile | Glu | Gln | Ile | Phe | Arg | Thr | Lys | Tyr | Asn | Asp | Ser | His | Val |      |
|     |     | 355 |     |     |     |     | 360 |     |     |     |     | 365 |     |     |     |      |

| AAG | GTT | GGA | CAT | GTA | CAA | TAT | TTC | TTG | GCT | CTC | GGG | GGA | TTT | ATT | GTA | 1508 |
|-----|-----|-----|-----|-----|-----|-----|-----|-----|-----|-----|-----|-----|-----|-----|-----|------|
| Lys | Val | Gly | His | Val | Gln | Tyr | Phe | Leu | Ala | Leu | Gly | Gly | Phe | Ile | Val |      |
|     |     | 370 |     |     |     |     | 375 |     |     |     |     | 380 |     |     |     |      |

| GCA | TAT | CAG | CCT | GTT | CTA | TCC | AAA | TCC | CTG | GCT | CAT | ATG | TAC | CTC | AGA | 1556 |
|-----|-----|-----|-----|-----|-----|-----|-----|-----|-----|-----|-----|-----|-----|-----|-----|------|
| Ala | Tyr | Gln | Pro | Val | Leu | Ser | Lys | Ser | Leu | Ala | His | Met | Tyr | Leu | Arg |      |
| 385 |     |     |     |     | 390 |     |     |     |     | 395 |     |     |     |     | 400 |      |

| GAA | TTG | ATG | AGA | GAC | AAC | AGG | ACC | GAT | GAG | ATG | CTC | GAC | CTG | GTA | AAC | 1604 |
|-----|-----|-----|-----|-----|-----|-----|-----|-----|-----|-----|-----|-----|-----|-----|-----|------|
| Glu | Leu | Met | Arg | Asp | Asn | Arg | Thr | Asp | Glu | Met | Leu | Asp | Leu | Val | Asn |      |
|     |     |     |     | 405 |     |     |     |     | 410 |     |     |     |     | 415 |     |      |

| AAT | AAG | CAT | GCA | ATT | TAT | AAG | AAA | AAT | GCT | ACC | TCA | TTG | TCA | CGA | TTG | 1652 |
|-----|-----|-----|-----|-----|-----|-----|-----|-----|-----|-----|-----|-----|-----|-----|-----|------|
| Asn | Lys | His | Ala | Ile | Tyr | Lys | Lys | Asn | Ala | Thr | Ser | Leu | Ser | Arg | Leu |      |
|     |     |     | 420 |     |     |     |     | 425 |     |     |     |     | 430 |     |     |      |

| | | | | | | | | | | | | | | | | |
|---|---|---|---|---|---|---|---|---|---|---|---|---|---|---|---|---|
| CGG | CGA | GAT | ATT | CGA | AAT | GCA | CCA | AAT | AGA | AAA | ATA | ACA | TTA | GAC | GAC | 1700 |
| Arg | Arg | Asp 435 | Ile | Arg | Asn | Ala | Pro 440 | Asn | Arg | Lys | Ile | Thr 445 | Leu | Asp | Asp | |
| ACA | ACA | GCT | ATT | AAA | TCG | ACA | TCG | TCT | GTT | CAA | TTC | GCC | ATG | CTC | CAA | 1748 |
| Thr | Thr 450 | Ala | Ile | Lys | Ser | Thr 455 | Ser | Ser | Val | Gln | Phe 460 | Ala | Met | Leu | Gln | |
| TTT | CTT | TAT | GAT | CAT | ATA | CAA | ACC | CAT | ATT | AAT | GAT | ATG | TTT | AGT | AGG | 1796 |
| Phe 465 | Leu | Tyr | Asp | His 470 | Ile | Gln | Thr | His | Ile 475 | Asn | Asp | Met | Phe | Ser | Arg 480 | |
| ATT | GCC | ACA | GCT | TGG | TGC | GAA | TTG | CAG | AAT | AGA | GAA | CTT | GTT | TTA | TGG | 1844 |
| Ile | Ala | Thr | Ala | Trp 485 | Cys | Glu | Leu | Gln | Asn 490 | Arg | Glu | Leu | Val | Leu 495 | Trp | |
| | CAC | GAA | GGG | ATA | AAG | ATT | AAT | CCT | AGC | GCT | ACA | GCG | AGT | GCA | ACA | TTA | 1892 |
| | His | Glu | Gly | Ile 500 | Lys | Ile | Asn | Pro | Ser 505 | Ala | Thr | Ala | Ser | Ala 510 | Thr | Leu | |
| GGA | AGG | AGA | GTG | GCT | GCA | AAG | ATG | TTG | GGG | GAT | GTC | GCT | GCT | GTA | TCG | 1940 |
| Gly | Arg | Arg 515 | Val | Ala | Ala | Lys | Met 520 | Leu | Gly | Asp | Val | Ala 525 | Ala | Val | Ser | |
| AGC | TGC | ACT | GCT | ATA | GAT | GCG | GAA | TCC | GTC | ACT | TTG | CAA | AAT | TCT | ATG | 1988 |
| Ser | Cys 530 | Thr | Ala | Ile | Asp | Ala 535 | Glu | Ser | Val | Thr | Leu 540 | Gln | Asn | Ser | Met | |
| CGA | GTT | ATC | ACA | TCC | ACT | AAT | ACA | TGT | TAT | AGC | CGA | CCA | TTG | GTT | CTA | 2036 |
| Arg 545 | Val | Ile | Thr | Ser | Thr 550 | Asn | Thr | Cys | Tyr | Ser 555 | Arg | Pro | Leu | Val | Leu 560 | |
| TTT | TCA | TAT | GGA | GAA | AAC | CAA | GGA | AAC | ATA | CAG | GGA | CAA | CTC | GGT | GAA | 2084 |
| Phe | Ser | Tyr | Gly | Glu 565 | Asn | Gln | Gly | Asn | Ile 570 | Gln | Gly | Gln | Leu | Gly 575 | Glu | |
| AAC | AAC | GAG | TTG | CTT | CCA | ACG | CTA | GAG | GCT | GTA | GAG | CCA | TGC | TCG | GCT | 2132 |
| Asn | Asn | Glu | Leu 580 | Leu | Pro | Thr | Leu | Glu 585 | Ala | Val | Glu | Pro | Cys 590 | Ser | Ala | |
| AAT | CAT | CGT | AGA | TAT | TTT | CTG | TTT | GGA | TCC | GGT | TAT | GCT | TTA | TTT | GAA | 2180 |
| Asn | His | Arg 595 | Arg | Tyr | Phe | Leu | Phe 600 | Gly | Ser | Gly | Tyr | Ala 605 | Leu | Phe | Glu | |
| AAC | TAT | AAT | TTT | GTT | AAG | ATG | GTA | GAC | GCT | GCC | GAT | ATA | CAG | ATT | GCT | 2228 |
| Asn | Tyr | Asn 610 | Phe | Val | Lys | Met 615 | Val | Asp | Ala | Ala | Asp 620 | Ile | Gln | Ile | Ala | |
| AGC | ACA | TTT | GTC | GAG | CTT | AAT | CTA | ACC | CTG | CTA | GAA | GAT | CGG | GAA | ATT | 2276 |
| Ser 625 | Thr | Phe | Val | Glu | Leu 630 | Asn | Leu | Thr | Leu | Leu 635 | Glu | Asp | Arg | Glu | Ile 640 | |
| TTG | CCT | TTA | TCC | GTT | TAC | ACA | AAA | GAA | GAG | TTG | CGT | GAT | GTT | GGT | GTA | 2324 |
| Leu | Pro | Leu | Ser | Val 645 | Tyr | Thr | Lys | Glu | Glu 650 | Leu | Arg | Asp | Val | Gly 655 | Val | |
| TTG | GAT | TAT | GCA | GAA | GTA | GCT | CGC | CGC | AAT | CAA | CTA | CAT | GAA | CTT | AAA | 2372 |
| Leu | Asp | Tyr | Ala 660 | Glu | Val | Ala | Arg | Arg 665 | Asn | Gln | Leu | His | Glu 670 | Leu | Lys | |
| TTT | TAT | GAC | ATA | AAC | AAA | GTA | ATA | GAA | GTG | GAT | ACA | AAT | TAC | GCG | TTT | 2420 |
| Phe | Tyr | Asp 675 | Ile | Asn | Lys | Val | Ile 680 | Glu | Val | Asp | Thr | Asn 685 | Tyr | Ala | Phe | |
| ATG | AAC | GGT | TTG | GCC | GAA | TTG | TTT | AAC | GGT | ATG | GGT | CAG | GTA | GGG | CAA | 2468 |
| Met | Asn | Gly 690 | Leu | Ala | Glu | Leu 695 | Phe | Asn | Gly | Met | Gly 700 | Gln | Val | Gly | Gln | |
| | GCT | ATA | GGC | AAA | GTT | GTA | GTA | GGG | GCT | GCC | GGT | GCA | ATC | GTA | TCT | ACC | 2516 |
| | Ala | Ile | Gly | Lys 705 | Val | Val | Val | Gly | Ala 710 | Ala | Gly | Ala | Ile | Val 715 | Ser | Thr 720 | |
| ATA | TCT | GGT | GTC | TCT | GCT | TTC | ATG | TCA | AAT | CCC | TTT | GGG | GCT | TTG | GCA | 2564 |
| Ile | Ser | Gly | Val | Ser 725 | Ala | Phe | Met | Ser | Asn 730 | Pro | Phe | Gly | Ala | Leu 735 | Ala | |
| ATC | GGT | TTA | ATC | ATT | ATA | GCA | GGA | CTC | GTG | GCT | GCA | TTT | TTA | GCA | TAT | 2612 |
| Ile | Gly | Leu | Ile | Ile 740 | Ile | Ala | Gly | Leu | Val 745 | Ala | Ala | Phe | Leu | Ala 750 | Tyr | |
| CGT | TAT | GTA | AAC | AAG | CTT | AAA | AGC | AAT | CCA | ATG | AAA | GCC | CTT | TAT | CCT | 2660 |
| Arg | Tyr | Val | Asn | Lys | Leu | Lys | Ser | Asn | Pro | Met | Lys | Ala | Leu | Tyr | Pro | |

```
                                       755                        760                         765
ATG  ACA  ACA  GAA  GTG  CTT  AAG  GCA  CAG  GCA  ACG  CGT  GAG  TTG  CAT  GGC     2708
Met  Thr  Thr  Glu  Val  Leu  Lys  Ala  Gln  Ala  Thr  Arg  Glu  Leu  His  Gly
     770                 775                      780

GAG  GAA  TCA  GAT  GAT  TTG  GAA  CGA  ACA  TCT  ATT  GAT  GAA  AGA  AAA  TTA     2756
Glu  Glu  Ser  Asp  Asp  Leu  Glu  Arg  Thr  Ser  Ile  Asp  Glu  Arg  Lys  Leu
785                      790                      795                      800

GAA  GAA  GCT  AGA  GAA  ATG  ATA  AAA  TAT  ATG  GCG  TTA  GTC  TCC  GCG  GAA     2804
Glu  Glu  Ala  Arg  Glu  Met  Ile  Lys  Tyr  Met  Ala  Leu  Val  Ser  Ala  Glu
                         805                      810                 815

GAA  CGC  CAC  GAG  AAA  AAA  CTG  CGG  AGA  AAG  AGG  CGA  GGC  ACT  ACC  GCC     2852
Glu  Arg  His  Glu  Lys  Lys  Leu  Arg  Arg  Lys  Arg  Arg  Gly  Thr  Thr  Ala
               820                      825                      830

GTT  CTA  TCG  GAC  CAC  CTG  GCA  AAA  ATG  AGG  ATT  AAA  AAT  AGT  AAC  CCT     2900
Val  Leu  Ser  Asp  His  Leu  Ala  Lys  Met  Arg  Ile  Lys  Asn  Ser  Asn  Pro
          835                      840                      845

AAA  TAT  GAT  AAG  TTA  CCT  ACT  ACA  TAT  TCA  GAC  TCA  GAA  GAT  GAT  GCT     2948
Lys  Tyr  Asp  Lys  Leu  Pro  Thr  Thr  Tyr  Ser  Asp  Ser  Glu  Asp  Asp  Ala
     850                      855                      860

GTG  TAAGTGGGCA  CTATTATATT  TGAACTGAAT  AAAACGCATA  GAGCATGATA                     3001
Val
865

TGGTTTACTC  ATTTATTGCG  AGATATAAAG  CATATTCAAT  ACGATATATT  GCGAACGTGA              3061

TGCTAAAAAC  ATAGCTCCCT  GTATTATTGA  TGCGCCATCA  TTTGATTAAT  AAATACATCG              3121

ACGCCGGCAT  CACTGGTGCG  GTGTATACCA  GCTACGGCGC  TAGCATTCAT  GGTATCCCGT              3181

GATTGCTCGA  TGCTTTCCTT  CTGAATTC                                                    3209
```

( 2 ) INFORMATION FOR SEQ ID NO:13:

( i ) SEQUENCE CHARACTERISTICS:
        ( A ) LENGTH: 865 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met  His  Tyr  Phe  Arg  Arg  Asn  Cys  Ile  Phe  Phe  Leu  Ile  Val  Ile  Leu
1                   5                        10                      15

Tyr  Gly  Thr  Asn  Ser  Ser  Pro  Ser  Thr  Gln  Asn  Val  Thr  Ser  Arg  Glu
               20                       25                      30

Val  Val  Ser  Ser  Val  Gln  Leu  Ser  Glu  Glu  Glu  Ser  Thr  Phe  Tyr  Leu
          35                        40                      45

Cys  Pro  Pro  Pro  Val  Gly  Ser  Thr  Val  Ile  Arg  Leu  Glu  Pro  Pro  Arg
     50                       55                      60

Lys  Cys  Pro  Glu  Pro  Arg  Lys  Ala  Thr  Glu  Trp  Gly  Glu  Gly  Ile  Ala
65                  70                       75                          80

Ile  Leu  Phe  Lys  Glu  Asn  Ile  Ser  Pro  Tyr  Lys  Phe  Lys  Val  Thr  Leu
               85                       90                      95

Tyr  Tyr  Lys  Asn  Ile  Ile  Gln  Thr  Thr  Trp  Thr  Gly  Thr  Thr  Tyr
               100                      105                     110

Arg  Gln  Ile  Thr  Asn  Arg  Tyr  Thr  Asp  Arg  Thr  Pro  Val  Ser  Ile  Glu
               115                      120                     125

Glu  Ile  Thr  Asp  Leu  Ile  Asp  Gly  Lys  Gly  Arg  Cys  Ser  Ser  Lys  Ala
     130                      135                     140

Arg  Tyr  Leu  Arg  Asn  Asn  Val  Tyr  Val  Glu  Ala  Phe  Asp  Arg  Asp  Ala
145                 150                      155                         160

Gly  Glu  Lys  Gln  Val  Leu  Leu  Lys  Pro  Ser  Lys  Phe  Asn  Thr  Pro  Glu
               165                      170                     175
```

```
Ser Arg Ala Trp His Thr Thr Asn Glu Thr Tyr Thr Val Trp Gly Ser
            180                 185                 190
Pro Trp Ile Tyr Arg Thr Gly Thr Ser Val Asn Cys Ile Val Glu Glu
        195                 200                 205
Met Asp Ala Arg Ser Val Phe Pro Tyr Ser Tyr Phe Ala Met Ala Asn
    210                 215                 220
Gly Asp Ile Ala Asn Ile Ser Pro Phe Tyr Gly Leu Ser Pro Pro Glu
225                 230                 235                 240
Ala Ala Ala Glu Pro Met Gly Tyr Pro Gln Asp Asn Phe Lys Gln Leu
                245                 250                 255
Asp Ser Tyr Phe Ser Met Asp Leu Asp Lys Arg Arg Lys Ala Ser Leu
            260                 265                 270
Pro Val Lys Arg Asn Phe Leu Ile Thr Ser His Phe Thr Val Gly Trp
        275                 280                 285
Asp Trp Ala Pro Lys Thr Thr Arg Val Cys Ser Met Thr Lys Trp Lys
    290                 295                 300
Glu Val Thr Glu Met Leu Arg Ala Thr Val Asn Gly Arg Tyr Arg Phe
305                 310                 315                 320
Met Ala Arg Glu Leu Ser Ala Thr Phe Ile Ser Asn Thr Thr Glu Phe
                325                 330                 335
Asp Pro Asn Arg Ile Ile Leu Gly Gln Cys Ile Lys Arg Glu Ala Glu
            340                 345                 350
Ala Ala Ile Glu Gln Ile Phe Arg Thr Lys Tyr Asn Asp Ser His Val
        355                 360                 365
Lys Val Gly His Val Gln Tyr Phe Leu Ala Leu Gly Gly Phe Ile Val
    370                 375                 380
Ala Tyr Gln Pro Val Leu Ser Lys Ser Leu Ala His Met Tyr Leu Arg
385                 390                 395                 400
Glu Leu Met Arg Asp Asn Arg Thr Asp Glu Met Leu Asp Leu Val Asn
                405                 410                 415
Asn Lys His Ala Ile Tyr Lys Lys Asn Ala Thr Ser Leu Ser Arg Leu
            420                 425                 430
Arg Arg Asp Ile Arg Asn Ala Pro Asn Arg Lys Ile Thr Leu Asp Asp
        435                 440                 445
Thr Thr Ala Ile Lys Ser Thr Ser Ser Val Gln Phe Ala Met Leu Gln
    450                 455                 460
Phe Leu Tyr Asp His Ile Gln Thr His Ile Asn Asp Met Phe Ser Arg
465                 470                 475                 480
Ile Ala Thr Ala Trp Cys Glu Leu Gln Asn Arg Glu Leu Val Leu Trp
                485                 490                 495
His Glu Gly Ile Lys Ile Asn Pro Ser Ala Thr Ala Ser Ala Thr Leu
            500                 505                 510
Gly Arg Arg Val Ala Ala Lys Met Leu Gly Asp Val Ala Ala Val Ser
        515                 520                 525
Ser Cys Thr Ala Ile Asp Ala Glu Ser Val Thr Leu Gln Asn Ser Met
    530                 535                 540
Arg Val Ile Thr Ser Thr Asn Thr Cys Tyr Ser Arg Pro Leu Val Leu
545                 550                 555                 560
Phe Ser Tyr Gly Glu Asn Gln Gly Asn Ile Gln Gly Gln Leu Gly Glu
                565                 570                 575
Asn Asn Glu Leu Leu Pro Thr Leu Glu Ala Val Glu Pro Cys Ser Ala
            580                 585                 590
Asn His Arg Arg Tyr Phe Leu Phe Gly Ser Gly Tyr Ala Leu Phe Glu
        595                 600                 605
```

```
Asn  Tyr  Asn  Phe  Val  Lys  Met  Val  Asp  Ala  Ala  Ile  Gln  Ile  Ala
     610                 615                 620

Ser  Thr  Phe  Val  Glu  Leu  Asn  Leu  Thr  Leu  Leu  Glu  Asp  Arg  Glu  Ile
625                      630                 635                      640

Leu  Pro  Leu  Ser  Val  Tyr  Thr  Lys  Glu  Glu  Leu  Arg  Asp  Val  Gly  Val
                    645                 650                      655

Leu  Asp  Tyr  Ala  Glu  Val  Ala  Arg  Arg  Asn  Gln  Leu  His  Glu  Leu  Lys
               660                      665                 670

Phe  Tyr  Asp  Ile  Asn  Lys  Val  Ile  Glu  Val  Asp  Thr  Asn  Tyr  Ala  Phe
          675                      680                      685

Met  Asn  Gly  Leu  Ala  Glu  Leu  Phe  Asn  Gly  Met  Gly  Gln  Val  Gly  Gln
     690                 695                      700

Ala  Ile  Gly  Lys  Val  Val  Val  Gly  Ala  Ala  Gly  Ala  Ile  Val  Ser  Thr
705                      710                 715                      720

Ile  Ser  Gly  Val  Ser  Ala  Phe  Met  Ser  Asn  Pro  Phe  Gly  Ala  Leu  Ala
                    725                 730                      735

Ile  Gly  Leu  Ile  Ile  Ile  Ala  Gly  Leu  Val  Ala  Ala  Phe  Leu  Ala  Tyr
               740                 745                      750

Arg  Tyr  Val  Asn  Lys  Leu  Lys  Ser  Asn  Pro  Met  Lys  Ala  Leu  Tyr  Pro
          755                      760                 765

Met  Thr  Thr  Glu  Val  Leu  Lys  Ala  Gln  Ala  Thr  Arg  Glu  Leu  His  Gly
      770                      775                      780

Glu  Glu  Ser  Asp  Asp  Leu  Glu  Arg  Thr  Ser  Ile  Asp  Glu  Arg  Lys  Leu
785                      790                 795                      800

Glu  Glu  Ala  Arg  Glu  Met  Ile  Lys  Tyr  Met  Ala  Leu  Val  Ser  Ala  Glu
                    805                 810                      815

Glu  Arg  His  Glu  Lys  Lys  Leu  Arg  Arg  Lys  Arg  Arg  Gly  Thr  Thr  Ala
               820                      825                 830

Val  Leu  Ser  Asp  His  Leu  Ala  Lys  Met  Arg  Ile  Lys  Asn  Ser  Asn  Pro
          835                      840                 845

Lys  Tyr  Asp  Lys  Leu  Pro  Thr  Thr  Tyr  Ser  Asp  Ser  Glu  Asp  Asp  Ala
     850                 855                      860

Val
865
```

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CGAATTCGTC GAC                           13

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AATTGTCGAC GAATTCGAGC T                  21

-continued ( 2 ) INFORMATION FOR SEQ ID NO:16:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:16:

ACTCAATCAA TAGCAATCAT GCACTATTTT AGGC 34

( 2 ) INFORMATION FOR SEQ ID NO:17:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:17:

GCGGAATTGC ATATTTTTCC TTATAG 26

( 2 ) INFORMATION FOR SEQ ID NO:18:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:18:

GGGATCCAAT CATGCACTAT TTTAGG 26

( 2 ) INFORMATION FOR SEQ ID NO:19:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:19:

CCATATATAT TCCCTACTAT TCCCCGCGGC GGTTCTAGAC 40